US012713509B1

(12) United States Patent
Markwat et al.

(10) Patent No.: US 12,713,509 B1
(45) Date of Patent: Aug. 18, 2026

(54) LIGHTING PANEL AND A SYSTEM FOR CONTROLLING THE LIGHTING PANEL

(71) Applicant: Light Tree Ventures Holding B.V., Den Hague (NL)

(72) Inventors: Kim Laurens Markwat, Miami, FL (US); Alain Dijkstra, Amstelveen (NL); Michael Kasbergen, Schoonhoven (NL); Tomislav Jacob Hooij, Den Hague (NL)

(73) Assignee: Light Tree Ventures USA Holding Inc, Miami, FL (US)

( * ) Notice: Subject to any disclaimer, the term of this patent is extended or adjusted under 35 U.S.C. 154(b) by 14 days.

(21) Appl. No.: 19/053,458

(22) Filed: Feb. 14, 2025

(51) Int. Cl.
*H05B 47/175* (2020.01)
*A61N 5/06* (2006.01)

(52) U.S. Cl.
CPC .............. *H05B 47/196* (2024.01); *A61N 5/06* (2013.01)

(58) Field of Classification Search
None
See application file for complete search history.

(56) References Cited

U.S. PATENT DOCUMENTS 10,478,635 B1 * 11/2019 Nelson ................. A61N 5/0616
2017/0146203 A1 * 5/2017 Belaidi ................. F21V 21/005
2023/0012300 A1 * 1/2023 Belkowski ........... H05B 47/165
2023/0414962 A1 * 12/2023 Sawyer .................... A61N 5/06

* cited by examiner

*Primary Examiner* — Anh Q Tran
(74) *Attorney, Agent, or Firm* — Willie Jacques; Emanus LLC

(57) ABSTRACT

Embodiments of the present invention provide a lighting panel and a system and a method to control a plurality of lighting panels in a network. The lighting panel comprises one or more light source and a control unit that allows a user to set a Group ID, and one or more control parameters for the lighting panel, wherein a Flag value is when the one or more control parameters are updated for the lighting panel. The lighting panel further comprises a connection interface that enable the lighting panel to connect with a plurality of other lighting panels in a network to transceive information on the Group ID, the Flag value and the one or more control parameters for the lighting panel. The control unit compares the Flag value of the lighting panel and adopt the one or more control parameters with a higher flag value.

21 Claims, 12 Drawing Sheets

900B

LIGHTING PANEL AND A SYSTEM FOR CONTROLLING THE LIGHTING PANEL

TECHNICAL FIELD

The present invention relates generally to a lighting panel. More specifically, the present invention relates to a system and a method for controlling communication between the lighting panels.

BACKGROUND ART

LED lighting panels have revolutionized the lighting industry with their energy efficiency, versatility, and sleek design. Lighting panels play a crucial role in modern lighting design, providing efficient and aesthetically pleasing illumination in various settings. Lighting panels find their use in offices, hospitals, supermarkets, restaurants, fitness rooms, etc. The lighting panels are generally used for enhancing the working environment. Various control parameters can be regulated for implementing the desired effect, such as color temperature, brightness, glare value, wavelength, intensity, and mode (pulsed or continuous).

Apart from use in the lighting industry for providing illumination effects, the lighting panels are also used in phototherapy and photobiomodulation therapy to treat various disease conditions by using specific light on the skin of a user. Phototherapy or photobiomodulation therapy is used to treat disorders and in the cosmetics field, such as to treat acne, wrinkles, redness, and scars.

The lighting panels used in phototherapy or photobiomodulation therapy are generally miniaturized versions of phototherapy panels used in the lighting industry, to target specific areas of a user's skin.

In the lighting industry and phototherapy or photobiomodulation therapy, a plurality of lighting panels are used to provide effective lighting conditions or treatment regimes. In order to get the desired effect, each lighting panel needs to operate with specific parameters, and sometimes a group of lighting panels operates with one set of parameters, and other lighting panels operate with another set of parameters.

Currently, each of the lighting panels is controlled by providing inputs manually with the desired set of parameters. There are certain methods known in the art where the user can make one of the lighting panels as a master device, such that the other device in the network acts as a slave device and follows the control parameters of the slave device. However, the conventional method has a disadvantage in that all the devices in the network follow the same control parameter of the master device. This is not desirable in situations where some of the panels need to operate with different control parameters and some with other control parameters. Moreover, in a master-slave configuration, one device becomes a master device, and every time controls need to be input in the particular master device.

U.S. Pat. No. 10,478,635 discloses a conventional photobiomodulation therapy system and method. The photobiomodulation therapy system comprises a plurality of light therapy devices connected via a wired connection, wherein one of the light therapy devices operates in a lead mode and all other devices operate in a follow mode. The system is configured to operate in lead or follow mode by selecting a physical lead and follow switch which only allows to flow of a unidirectional control signal. The light therapy devices in follow mode perform operations as instructed by the light therapy device in the lead mode. The system of U.S. Pat. No. 10,478,635 suffers from various limitations, as the system is a centralized control structure based on master-slave configuration. The parameters update logic is based on master-initiated and globally executed, and the communication is unidirectional which means only one master device is assigned at a time which can control other slave devices. Also, If the master device fails, it halts the operation of parameters updation in all the slave devices, hence the system is rigid and requires configuring a master device every time. Another limitation of the control system is that in lead follow mode (master-slave configuration), all the slave device follows the control parameters of the master device and if at a later stage, a change is made in another slave device, the updation of control parameters in the system gets failed to execute.

US20230414962 discloses another conventional light therapy system that includes a remote control device and a plurality of light therapy devices. The light therapy device operates in a standalone mode and a cumulative mode where operating instructions are distinct and individual for each light therapy device, to permit identical or different operation between devices. The system of US20230414962 suffers from the limitation that each of the connected light therapy devices needs to be commanded individually using a remote control for updating the control parameters. Updating control parameters individually for each lighting panel is not feasible and the chances of missing out are large.

In order to overcome the limitations associated with prior art, the present invention provides a lighting panel and a system to control communication between the lighting panels.

OBJECTS OF THE INVENTION

Some of the objects of the invention are as follows:

An object of the present invention is to provide a lighting panel that is able to propagate changes made in the control panel to other lighting panels;

Another object of the present invention is to provide a system for controlling a plurality of lighting panels in a network.

Another object of the invention is to provide a system to propagate changes made in one lighting panel to other lighting panels in the network.

Another object of the present invention is to provide a system to assign Group ID to a plurality of lighting panels in the network to propagate changes in other lighting panels.

Another object of the present invention is to provide a method for controlling a plurality of lighting panels in a network.

Another object of the invention is to provide a method to propagate changes made in one lighting panel to other lighting panels in the network.

Another object of the present invention is to provide a method to assign Group ID to a plurality of lighting panels in the network to propagate changes in other lighting panels.

SUMMARY OF THE INVENTION

According to a first aspect of the present invention, a lighting panel is provided. The lighting panel comprising: one or more light sources; a control unit that allows a user to set one or more control parameters for the lighting panel, wherein a Flag value is updated when the one or more control parameters are modified for the lighting panel; a connection interface that enables the lighting panel to connect with a plurality of other lighting panels in a network to transceive data corresponding to the Flag value and the one or more control parameters; and wherein the control unit compares the Flag value of the lighting panel with the flag value received from each of the plurality of other lighting panels to identify a highest flag value lighting panel and adopts the one or more control parameters associated with the highest flag value lighting panel.

In one embodiment of the invention, the one or more light sources is a therapeutic light source.

In one embodiment of the invention, the lighting panel is assigned with a Group ID such that the lighting panel forms a same group with a plurality of lighting panels having the Group ID with same value.

According to a second aspect of the present invention, a lighting panel is provided. The lighting panel comprising: one or more light sources; a control unit that allows a user to set a Group ID, a Flag value, and one or more control parameters for the lighting panel; a connection interface that enables the lighting panel to connect with a plurality of other lighting panels in a network to transceive data corresponding to the Group ID, the Flag value, and the one or more control parameters for the lighting panel; and wherein the control unit compares the Flag value of the lighting panel and the Flag value received from each of the plurality of other lighting panels having the Group ID same as of the Group ID of the lighting panel, identifies a highest flag value lighting panel and adopts the one or more control parameters associated with the highest flag value lighting panel.

In one embodiment of the invention, the lighting panel is configured to connect with an external device to monitor and update the one or more control parameters of the lighting panel.

According to a third aspect of the present invention, a lighting panel is provided. The lighting panel comprising: one or more light sources; a control unit that allows a user to set a Group ID, and one or more control parameters for the lighting panel, wherein each of the one or more control parameters is associated with a corresponding flag value; a connection interface that enables the lighting panel to connect with a plurality of other lighting panels in a network to transceive data corresponding to the Group ID, the Flag value, and the one or more control parameters for the lighting panel; and wherein the control unit compares the corresponding flag value for each of the one or more control parameters of the lighting panel and the flag value for each of the one or more control parameters received from each of the plurality of other lighting panels having the Group ID same as of the Group ID of the lighting panel, identifies one or more lighting panels having highest flag value for each of the one or more control parameters and adopts each of the one or more control parameters associated with the one or more lighting panels having highest flag value.

In one embodiment of the invention, the lighting panel further comprises one or more sensors for monitoring parameters of a target surface and the lighting panel, and the control unit communicate the ambient conditions to the plurality of lighting panels in the network and to the wireless device.

According to a fourth aspect of the present invention, a lighting panel control system is provided. The lighting panel control system comprising: a network of a plurality of lighting panels, each of the plurality of lighting panels comprising: a control unit that allows a user to set a one or more control parameters for the lighting panel, wherein a Flag value is when the one or more control parameters are updated; a connection interface that enables each of the plurality of lighting panels to connect with each other to transceive data corresponding to the Flag value and the one or more control parameters for the lighting panel; wherein each of the plurality of lighting panels acts as a node in the network; and wherein each of the plurality of lighting panels compares the flag value for the plurality of lighting panels to identify a highest flag value lighting panel and adopts the one or more control parameters associated with the highest flag value lighting panel.

In one embodiment of the invention, the network is a wireless or wired network.

In one embodiment of the invention, each of the plurality of lighting panels is assigned with a Group ID such that each of the plurality of lighting panels having the Group ID with same value are assigned to a same group.

In one embodiment of the invention, the flag value is compared and the one or more control parameters are updated for each of the plurality of lighting panels assigned in the same group.

According to a fifth aspect of the present invention, a lighting panel control system is provided. The lighting panel control system comprising: a network of a plurality of lighting panels, each of the plurality of lighting panels comprising: one or more light sources; a control unit that allows a user to set a Group ID, a Flag value, and one or more control parameters; a connection interface that enables each of the plurality of lighting panels to connect with each other to transceive data corresponding to the Group ID, the Flag value, and the one or more control parameters for the lighting panel; wherein each of the plurality of lighting panels acts as a node in the network and each of the plurality of lighting panels with a value of the Group ID same are identified as a member of a same group; and wherein each of the members of the same group compares the Flag value of the member of the same group to identify a highest flag value lighting panel and adopts the one or more control parameters associated with the highest flag value lighting panel.

In one embodiment of the invention, the network is wireless or wired network.

According to a sixth aspect of the present invention, a lighting panel control system is provided. The lighting panel control system comprising: a network of a plurality of lighting panels to exchange data between each of the plurality of lighting panels; wherein each of the plurality of lighting panels comprises: a connection interface to connect with each of the plurality of lighting panels in the network; a control unit that allows a user to set a Group ID, and one or more control parameters for the lighting panel, wherein each of the one or more control parameters is associated with a corresponding flag value; wherein each of the plurality of lighting panels acts as a node in the network and each of the plurality of lighting panels with a value of the Group ID same are identified as a member of a same group; and wherein the control unit in each of the plurality of lighting panels is configured to: monitor the flag value corresponding to each of the one or more control parameters of the members of the same group; identify, for each of the one or more control parameters, a highest flag value member; and adopt each of the one or more control parameters associated with the highest flag value member.

In one embodiment of the invention, the one or more control parameters comprises intensity, wavelength, frequency, duty cycle, pulse width, power, duration, dosage, rate of emission, and mode.

In one embodiment of the invention, one of the one or more control parameters is intensity of light, and is associated with a first flag value such that each of the plurality of lighting panels monitors for a highest first flag value and updates the intensity of light for each of the plurality of lighting panel corresponding to value of one or more control parameter with the highest first flag value.

In one embodiment of the invention, one of the one or more control parameters is wavelength of light, and is associated with a second flag value such that each of the plurality of lighting panels monitors for a highest second flag value and update wavelength of light for each of the plurality of lighting panel corresponding to value of one or more control parameter with the highest second flag value.

According to a seventh aspect of the present invention, there is provided a method for controlling a plurality of lighting panels in a network. The method comprising: connecting the plurality of lighting panels in the network wherein each of the plurality of lighting panels acts as a node in the network and comprises a control unit; assigning a control parameter to each of the plurality of lighting panels, such that the control parameter is associated with a Flag value indicating a timestamp of updation of the control parameters; detecting in the network for a change in the Flag value for each of the plurality of lighting panels; comparing the Flag values of each of the plurality of lighting panels and identifying a highest flag value lighting panel; propagating the control parameter of the lighting panel with the flag values as highest to each of the plurality of lighting panels; and updating the control parameters of each of the plurality of lighting panels with the control parameters associated with the highest flag value lighting panel.

According to an eighth aspect of the present invention, there is provided a method for controlling a plurality of lighting panels within a network. The method comprising: connecting the plurality of lighting panels in the network, each of the plurality of lighting panels having one or more light sources, a control unit, and a connection interface to form the network wherein each of the plurality of lighting panels acts as a node; setting a Group ID in each of the plurality of lighting panels using the control unit such that each of the plurality of lighting panels having the same value of the Group ID is assigned to a same group; assigning a Flag value using the control unit to a control parameter for each of the plurality of lighting panels; monitoring, within the network, the Flag values of each of the plurality of lighting panels in the same group to identify a highest flag value lighting panel; and updating the control parameters of each of the plurality of lighting panels with the control parameters associated with highest flag value lighting panel.

According to a ninth aspect of the present invention, there is provided a method for controlling a plurality of lighting panels within a network. The method comprising: connecting the plurality of lighting panels in the network, each of the plurality of lighting panels having one or more light sources, a control unit, and a connection interface to form the network wherein each of the plurality of lighting panels acts as a node; setting a Group ID in each of the plurality of lighting panels using the control unit such that each of the plurality of lighting panels having same value of the Group ID is assigned to a same group; setting one or more control parameters using the control unit, wherein each of the one or more control parameters is associated with a flag value; monitoring, within the network, the Flag values of each of the one or more control parameters of each of the plurality of lighting panels in the same group; identifying a highest Flag value lighting panel for each of the one of the one or more control parameters; and updating the one of the one or more control parameters of each of the plurality of lighting panels with a value associated with the highest flag value lighting panel.

In the context of the specification, the term “processor” refers to one or more of a microprocessor, a microcontroller, a general-purpose processor, a Field Programmable Gate Array (FPGA) or an Application Specific Integrated Circuit (ASIC), and the like.

In the context of the specification, the phrase “memory unit” refers to volatile storage memory, such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc.

In the context of the specification, the phrase “storage device” refers to a non-volatile storage memory such as EPROM, EEPROM, flash memory, or the like.

In the context of the specification, the phrase “communication interface” refers to a device or a module enabling direct connectivity via wires and connectors such as USB, HDMI, VGA, or wireless connectivity such as Bluetooth or Wi-Fi, or Local Area Network (LAN) or Wide Area Network (WAN) implemented through TCP/IP, IEEE 802.x, GSM, CDMA, LTE, or other equivalent protocols.

In the context of the specification, the phrase “communication network” refers to a group of several connected devices including computing devices (such as desktops, mobile handheld devices, tablet PCs, notebooks, etc.), local and remotely located servers (such as web servers, application servers, database servers, Application Program Interface (API) servers, load balancers, compute nodes, and the like), routers, antennas, modems, multiplexers, demultiplexers, and the like. In that regard, the aforementioned connected devices may be able to exchange data signals through wired and/or wireless means as per several combinations of several different communication protocols such as 802.11 (Wi-Fi), 802.3 (Ethernet), Bluetooth, BLE, NFC, RFID, ZigBee, Wi-Fi HaLow, Z-Wave, LoRa (Long Range), Thread and 3GPP protocols such as HSPA, HSDPA, LTE, GSM, CDMA, WLL and the like.

In the context of this specification, terms like “light”, “radiation”, “irradiation”, “emission” and “illumination”, etc. refer to electromagnetic radiation in frequency ranges varying from the visible frequencies to Infrared (IR) frequencies and wavelengths, wherein the range is inclusive of visible light, and IR frequencies and wavelengths. Preferably, it refers to low level electromagnetic radiation of low level of red and near Infrared (NIR) light. It is to be noted here that IR radiation can be categorized into several categories according to respective wavelength ranges which are again envisaged to be within the scope of this invention. A commonly used subdivision scheme for IR radiation includes Near IR (0.75-1.4 μm), Short-Wavelength IR (1.4-3 μm), Mid-Wavelength IR (3-8 μm), Long-Wavelength IR (8-15 μm) and Far IR (15-1000 μm). In this regard, light application is at relatively low energy densities, typically below about 500 mW, as compared to other forms of laser therapy that are used for ablation, cutting, and thermally coagulating tissue. In some instance, the electromagnetic radiation can also be in wavelengths in the blue or ultraviolet regions, especially for treatment of conditions that occur at the skin surface, such as psoriasis or infection.

In the context of the specification, term “light source” or “phototherapy source” etc. refers to a source emitting coherent laser light, or light emitting diodes (“LEDs”). The term “light therapy” refers to light generated from any of the source, such as laser, LED sources or Super luminous diodes (“SLD”).

In the context of the specification, when an element is referred to as being “fixed to” or “disposed to” another element, it may either directly on another element or indirectly on that other element. When a component is said to be "connected" or "connected to" another component, it may be directly connected to another component or indirectly connected to other component on the piece.

In the context of the specification, the terms "first", "second" and "third" are only used for descriptive purposes and do not implicate the relative importance or to implicitly indicate the quantity of technical features indicated.

In the context of the specification, the term "plurality" means two or more than two, unless otherwise indicated.

In the context of the specification, the term "several" means more than one, unless otherwise specified.

In the context of the specification, "Light Emitting Diodes (LEDs)" refer to semiconductor diodes capable of emitting electromagnetic radiation when supplied with an electric current. The LEDs are characterized by their superior power efficiencies, smaller sizes, rapidity in switching, physical robustness, and longevity when compared with incandescent or fluorescent lamps. In that regard, the one or more LEDs may be through-hole type LEDs (generally used to produce electromagnetic radiations of red, green, yellow, blue and white colors), Surface Mount Technology (SMT) LEDs, Bi-color LEDs, Pulse Width Modulated RGB (Red-Green-Blue) LEDs, and high-power LEDs, etc.

Materials used in the one or more LEDs may vary from one embodiment to another depending upon the frequency of radiation required. Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGaInP) based compositions, while blue, green, and cyan use Indium Gallium Nitride based compositions. White light may be produced by mixing red, green, and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultraviolet (UV) LEDs may be combined with europium-based phosphors to generate red and blue lights and copper and zinc doped zinc sulfide-based phosphor to generate green light.

In addition to conventional mineral-based LEDs, one or more LEDs may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on generation of OLED panels can be found in Bardsley, J. N (2004), "International OLED Technology Roadmap", IEEE Journal of Selected Topics in Quantum Electronics, Vol. 10, No. 1, that is included herein in its entirety, by reference. An exemplary description of flexible inorganic light-emitting diode strips can be found in granted U.S. Pat. No. 7,476,557 B2, titled "Roll-to-roll fabricated light sheet and encapsulated semiconductor circuit devices", which is included herein in its entirety, by reference.

In several embodiments, the one or more LEDs may also be micro-LEDs described through U.S. Pat. Nos. 8,809,126 B2, 8,846,457 B2, 8,852,467 B2, 8,415,879 B2, 8,877,101 B2, 9,018,833 B2 and their respective family members, assigned to NthDegree Technologies Worldwide Inc., which are included herein by reference, in their entirety. The one or more LEDs, in that regard, may be provided as a printable composition of the micro-LEDs, printed on a substrate.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

DETAILED DESCRIPTION

Figure 1A:
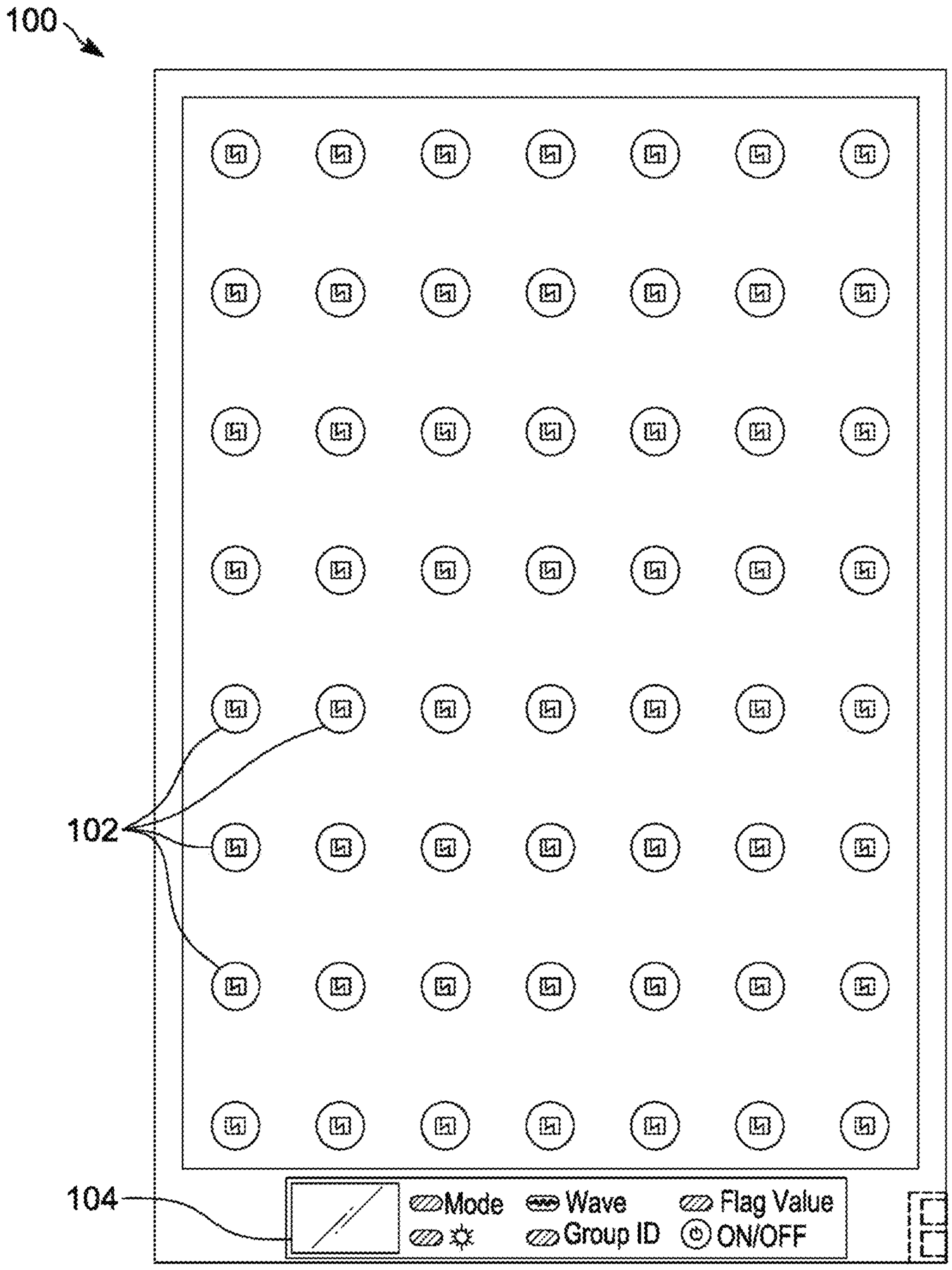
FIG. 1A illustrates configuration of a lighting panel in accordance with an embodiment of the present invention.

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

Embodiments of the present invention provide a lighting panel. The lighting panel comprises a plurality of LEDs and a control unit. The control unit allows a user to set certain control parameters, such as Group ID, wavelength, intensity, frequency, duty cycle, pulse width, power, duration/time, dosage, rate of emission, color, and mode etc. of the light emitted by the plurality of LEDs. The lighting panel has a connection interface that enables the lighting panel to connect with other panels in a network. The lighting panel is able to transmit and receive information on Group ID and control parameters with other lighting panels in the network. When a user alters the control parameters of the lighting panel, it gets associated with a Flag value, which denotes the timestamp value at which the changes in control parameters are done. Along with other information, the lighting panel transmits the Flag value of the lighting panel and receives the flag value of the control parameters of other lighting panels in the network. The Group ID is assigned to the lighting panel in order to allow the lighting panel to identify other lighting panels belonging to the same Group ID. When the lighting panel receives information on the control parameters of other lighting panels in the network, the lighting panel compares the Group ID of other lighting panels and considers the lighting panel with the same Group ID as that of the Group ID of the lighting panel belonging to the same group. The lighting panel then compares the Flag value of other lighting panels within the same group and identifies the lighting panel with the latest Flag value and copy the control parameters of the lighting panel with the latest Flag value in the control unit. The control unit then uses the copied control parameters and operates the plurality of LEDs with the copied control parameters.

In an embodiment of the present invention, the Group ID can be assigned default or it can be manually set by a user. When a lighting panel is powered on after being turned off, it initializes in default mode, operating with pre-set control parameters. During network setup, the user assigns a Group ID to the lighting panel, enabling it to establish a connection with other lighting panels sharing the same Group ID. Upon connection, all lighting panels in the network start with their default control parameter settings.

In some embodiments, the user can set the Flag value manually in the control unit of the lighting panel, such that the lighting panel has the latest Flag value and all the lighting panels with the same Group ID in the network follow the control parameters of the lighting panel. In some embodiments, there is a plurality of control parameters for operating the plurality of LEDs, such that each of the plurality of control parameters is associated with a flag value. In the network, the lighting panel compares the flag value for each of the plurality of control parameters. Each of the plurality of control parameters with the highest or latest flag value is copied by the lighting panel with the same group ID in the network.

The lighting panel can be a lighting source or it can be used for providing therapy to a user. Several additional functionalities may be incorporated into the lighting panel. The lighting panel can be connected to an external device to monitor and to set the plurality of control parameters, such as wavelength, intensity, frequency, duty cycle, pulse width, power, duration, dosage, rate of emission, color, illumination level, brightness value, mode, pulse frequency, etc. The lighting panel can be connected with other lighting panels through a wired or wireless network. The wireless network can be a mesh network or Bluetooth network. The lighting panel may further comprise one or more sensors for monitoring an ambient condition and the control unit of the lighting panel communicates the ambient environment conditions to the plurality of lighting panels in the network and/or to an external communication device connected with the network. Based on the feedback on the ambient condition, the user can modify the control parameters of the lighting panel using the external communication device. The one or more control parameters can be changed in the lighting panel based on the feedback received from the one or more sensors.

In an embodiment of the present invention, the lighting panel is in communication with other lighting panels in the network. The network includes but is not limited to RFID, NFC, MQTT, Z-wave, LoRa (Long Range), Thread, Wi-Fi HaLow, Zigbee, or BLE. In the network, the lighting panel broadcasts a signal containing information on flag values, group ID, one or more parameters, which is then received by other lighting panels in the network. Similarly, other lighting panels in the network also broadcast the signal with information on flag value, groupID, and one or more control parameters.

The communication between the two lighting panels is either direct or indirect. In case of direct communication, the lighting panel is directly connected to other lighting panel in the network. In case of indirect communication, a first lighting panel and a second lighting panel are located at a distance and are not connected directly, and a third lighting panel is in connection with both the first lighting panel and the second lighting panel. The first lighting panel and the second lighting panel communicates with each other through the third lighting panel. The first lighting panel broadcast the signal with information on Group ID, flag values and one or more control parameters in the network, and the third lighting panel receives the broadcast signal from the first lighting panel. The third lighting panel broadcast another signal containing information received from broadcast signal of the first lighting panel and the information of the third lighting panel. The second lighting panel is in communication with the third lighting panel receives the broadcast signal transmitted by the third lighting panel and receives information originally broadcasted by the first lighting panel.

In an embodiment, the lighting panel broadcast the signal and search for a broadcast signal transmitted by other lighting panels in the network at a pre-defined interval of time.

Embodiments of the present invention provide a system for controlling a plurality of lighting panels in a network. The system comprises a plurality of lighting panels connected in a wired or wireless network. Each of the plurality of lighting panels has one or more light sources and a control unit that allows a user to set a plurality of control parameters for the lighting panel. The control parameters that can be set by the control unit include but is not limited to Group ID, wavelength, intensity, frequency, duty cycle, pulse width, power duration, dosage, rate of emission, color, and mode of the light emitted by the plurality of LEDs etc. Each of the lighting panels in the network transmits or receives information on Group ID and control parameters with other lighting panels in the network. Each of the plurality of lighting panels in the network is assigned a Group ID, such that the lighting panels with the same Group ID form a same group. When a user modifies any of the control parameters of the lighting panel, the updated control parameters get associated with a Flag value that denotes the timestamp at which the changes in control parameters took place. Within the network, the system communicates the flag value and the control parameters with each of the plurality of lighting panels. Each of the lighting panel belonging to the same group compare the Flag value of the control parameters associated with other lighting panels and copies the control parameters with the latest or highest flag value and adjusts the control parameters of the lighting panel with the copied control parameters. The control parameter includes intensity, wavelength and mode of the plurality of LEDs.

In an embodiment, each of the plurality of control parameters is associated with a corresponding value and the lighting panels of the same group compare the flag value for each of the control parameters, and each of the control parameters is replaced with the control parameter having a corresponding higher flag value. For example, one of the control parameters is the intensity of light which is associated with a first flag value and another control parameter is the wavelength of light which is associated with a second flag value. Each of the lighting panels compares the first flag value and second flag value of all the lighting panels in the network, and adjusts the intensity of light with the corresponding intensity of light having a higher first flag value. Similarly, the wavelength of the lighting panel is replaced with the wavelength value having a corresponding higher second value.

In an embodiment of the present invention, the Group ID can be assigned default or it can be manually set by a user. When a lighting panel is powered on after being turned off, the lighting panel initializes in default mode. During network setup, the user assigns a Group ID to the lighting panel, enabling it to establish a connection with other lighting panels sharing the same Group ID. Upon connection, all lighting panels in the network start with their default control parameter settings. For instance, If a first lighting panel is operating with a first control parameter having a first value and a second control parameter with a second value is connected in a network with a second lighting panel operating with the first control parameter and the second control parameter with a value different than the first lighting panel, then upon connection, both the first lighting panel and the second lighting panel initializes with default values of the first control parameter and the second control parameter.

In an embodiment of the present invention, the user can assign different Group IDs to the plurality of lighting panel, so that each of the lighting panel operates independently of other lighting panels in the network.

In an embodiment of the present invention, the lighting panel is in communication with other lighting panels in the network. The network includes but is not limited to RFID, NFC, MQTT, Z-wave, LoRa (Long Range), Thread, Wi-Fi HaLow, Zigbee, or BLE. In the network, the lighting panel broadcasts a signal containing information on flag values, group ID, one or more parameters, which is then received by other lighting panels in the network. Similarly, other lighting panels in the network also broadcast the signal with information on flag value, groupID, and one or more control parameters.

The communication between the two lighting panels is either direct or indirect. In case of direct communication, the lighting panel is directly connected to other lighting panel in the network. In case of indirect communication, a first lighting panel and a second lighting panel are located at a distance and are not connected directly, and a third lighting panel is in connection with both the first lighting panel and the second lighting panel. The first lighting panel and the second lighting panel communicates with each other through the third lighting panel. The first lighting panel broadcast the signal with information on Group ID, flag values and one or more control parameters in the network, and the third lighting panel receives the broadcast signal from the first lighting panel. The third lighting panel broadcast another signal containing information received from broadcast signal of the first lighting panel and the information of the third lighting panel. The second lighting panel is in communication with the third lighting panel receives the broadcast signal transmitted by the third lighting panel and receives information originally broadcasted by the first lighting panel.

In an embodiment, the lighting panel broadcast the signal and search for a broadcast signal transmitted by other lighting panels in the network at a pre-defined interval of time.

In an embodiment of the present invention, the system can be used in fitness rooms, office spaces, commercial shops, phototherapy, and personal lighting systems. The office space has a plurality of lighting panels arranged throughout the space and each unit in the office space has different light intensity requirements. The system can be used to assign the same Group ID to particular lighting panels in a particular space. A user can update the control parameters in one lighting panel to update the control parameters of other lighting panels in the space. Similarly, for Phototherapy, some panels need to emit light of a specific wavelength and intensity. A user can control the lighting panels in the system by updating control parameters throughout the phototherapy system. Similarly, in the personal lighting system, such as a lighting system for doing make-up, the user can update control parameters in the lighting panels that are beyond the reach of the user.

Another embodiment of the present invention provides a method for controlling a plurality of lighting panels in a network. The method involves connecting a plurality of lighting panels in a network. The plurality of the lighting panel acts as a node in the network. Each of the plurality of lighting panels comprises a control unit and is assigned one or more control parameters for the operation of a light source in the lighting panel. Whenever the control parameters are updated, the updated control parameter is associated with a flag value indicating a timestamp of updating the control parameters. The method further involves detecting in the network for any change in the flag value for each of the plurality of lighting panels. The flag value of each of the plurality of lighting panels is compared to identify a lighting panel with the highest flag value. The control parameter with the highest flag value is propagated to each of the plurality of lighting panels, and the control parameters of each of the plurality of lighting panels are updated. The user may be able to assign a Group ID to each of the lighting panels such that the lighting panels with the same Group ID in the network belong to a same group. In this case, the flag value of the lighting panels within the same group are compared and the control parameters are updated in the lighting panels belonging to the same group. The user may also be able to alter the flag value manually to propagate the changes made in the lighting panel to other lighting panels in the group.

In an embodiment of the present invention, the Group ID can be assigned default or it can be manually set by a user. When a lighting panel is powered on after being turned off, the lighting panel initializes in default mode. During network setup, the user assigns a Group ID to the lighting panel, enabling it to establish a connection with other lighting panels sharing the same Group ID. Upon connection, all lighting panels in the network start with their default control parameter settings. For instance, If a first lighting panel is operating with a first control parameter having a first value and a second control parameter with a second value is connected in a network with a second lighting panel operating with the first control parameter and the second control parameter with a value different than the first lighting panel, then upon connection, both the first lighting panel and the second lighting panel initializes with default values of the first control parameter and the second control parameter.

In an embodiment of the present invention, the lighting panel is in communication with other lighting panels in the network. The network includes but is not limited to RFID, NFC, MQTT, Z-wave, LoRa (Long Range), Thread, Wi-Fi HaLow, Zigbee, or BLE. In the network, the lighting panel broadcasts a signal containing information on flag values, group ID, one or more parameters, which is then received by other lighting panels in the network. Similarly, other lighting panels in the network also broadcast the signal with information on flag value, groupID, and one or more control parameters.

The communication between the two lighting panels is either direct or indirect. In case of direct communication, the lighting panel is directly connected to other lighting panel in the network. In case of indirect communication, a first lighting panel and a second lighting panel are located at a distance and are not connected directly, and a third lighting panel is in connection with both the first lighting panel and the second lighting panel. The first lighting panel and the second lighting panel communicates with each other through the third lighting panel. The first lighting panel broadcast the signal with information on Group ID, flag values and one or more control parameters in the network, and the third lighting panel receives the broadcast signal from the first lighting panel. The third lighting panel broadcast another signal containing information received from broadcast signal of the first lighting panel and the information of the third lighting panel. The second lighting panel is in communication with the third lighting panel receives the broadcast signal transmitted by the third lighting panel and receives information originally broadcasted by the first lighting panel.

In an embodiment, the lighting panel broadcast the signal and search for a broadcast signal transmitted by other lighting panels in the network at a pre-defined interval of time.

Several embodiments of the present invention will now be explained regarding FIGS. 1A-9D.

FIG. 1A illustrates a configuration of a lighting panel in accordance with an embodiment of the present invention. The lighting panel 100 comprises one or more light source having a plurality of LEDs 102 arranged in an array. The lighting panel 100 has a control unit 104 to set one or more control parameters for the plurality of LEDs 102. The user interface 106 comprises a plurality of buttons for controlling the one or more control parameters for the plurality of LEDs 102. As shown in FIG. 1A, the control unit may include a power button 108, a mode button 110, a wavelength button 112, a flag value button 114, an intensity button 116, and a Group ID button 118. The lighting panel 100 further comprises a battery and a charging interface 120. The lighting panel 100 further comprises a connection interface that enables the lighting panel 100 to connect with other lighting panels in a network.

Figure 1B:
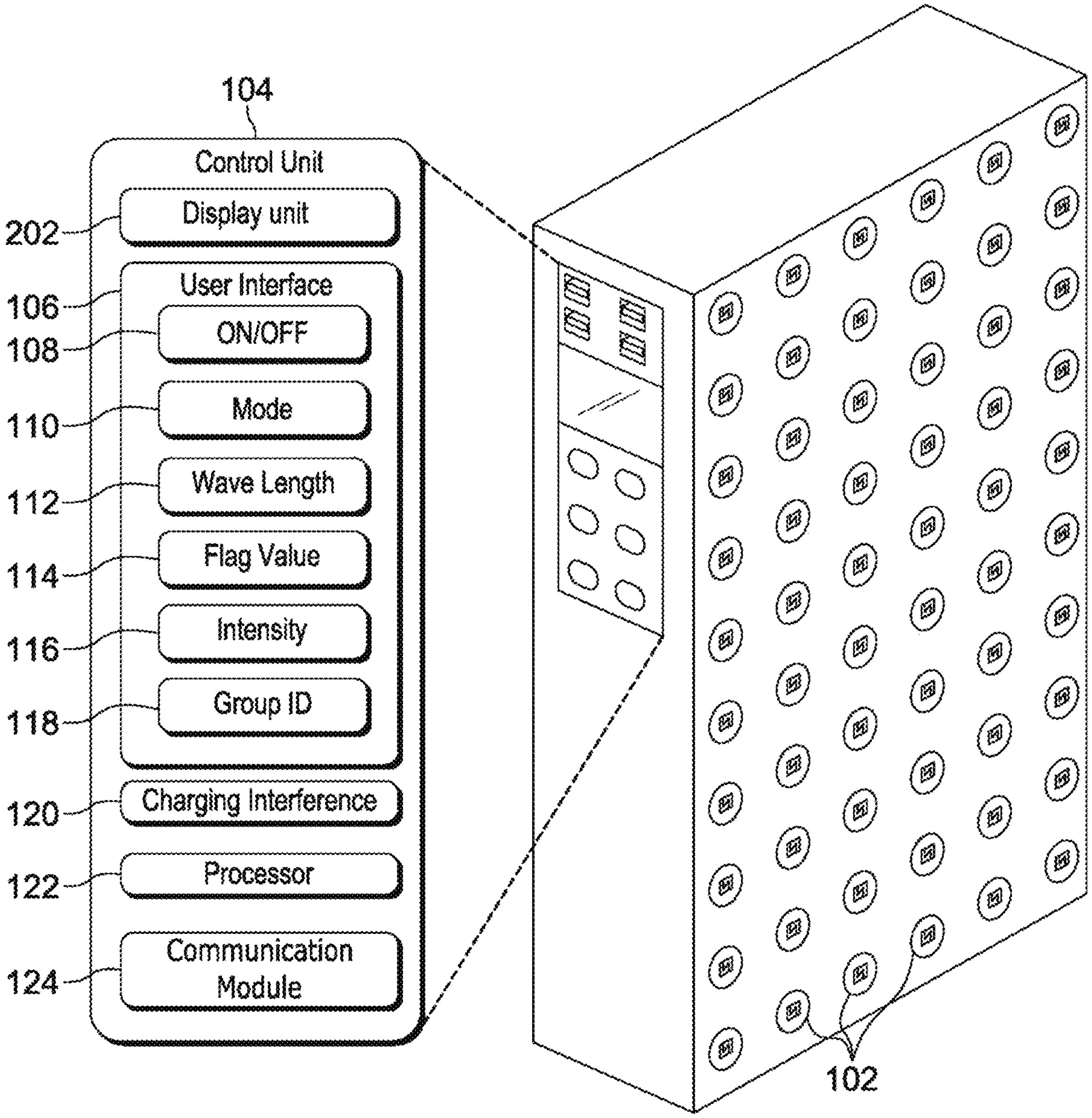
FIG. 1B shows another configuration of the lighting panel in accordance with an embodiment of the present invention.

FIG. 1B shows another configuration of the lighting panel in accordance with an embodiment of the present invention. As shown in FIG. 1B, the lighting panel 100 comprises a plurality of LEDs 102 arranged on the front surface of the lighting panel 100. The control unit 104 is provided on the side of the lighting panel 100. The control unit 104 comprises a processor 122, a user interface 106, and a communication module 124. The user interface 106 of the control unit 104 comprises a plurality of buttons for setting one or more control parameters for the plurality of LEDs 102. The plurality of buttons comprises the power button 108, the mode button 110, the wavelength button 112, the flag value button 114, the intensity button 116, and the Group ID button 118. The lighting panel 100 as shown in FIG. 1A and FIG. 1B can be in any shape suitable for providing the desired effect.

Figure 2:
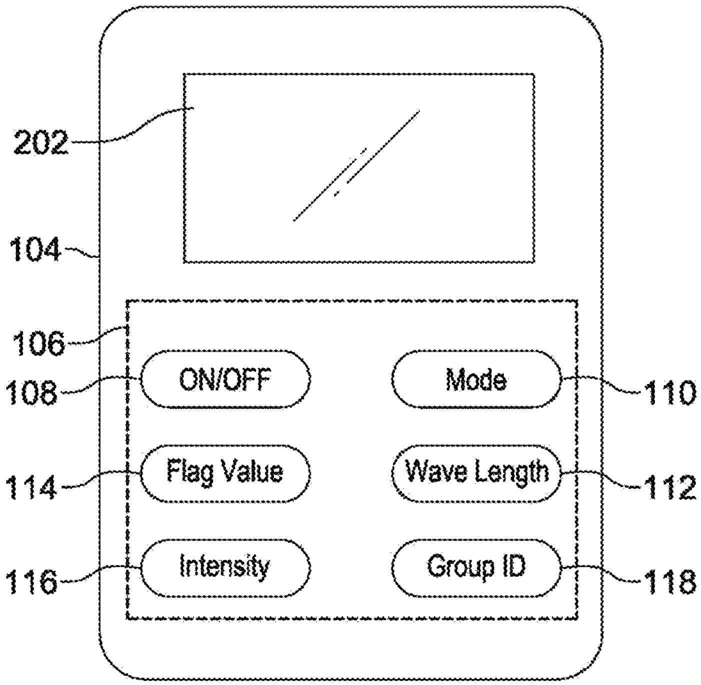
FIG. 2 illustrates the control unit of the lighting panel in accordance with an embodiment of the present invention.

FIG. 2 illustrates the control unit of the lighting panel in accordance with an embodiment of the present invention. The control unit 104 is positioned on the lighting panel 100 to monitor and regulate the control parameters of the plurality of LEDs 102. The control unit 104 comprises a display 202 for displaying the current control parameters of the plurality of LEDs 102, and one or more buttons for setting the one or more control parameters of the LEDs 102. The one or more buttons include the power button 108, the mode button 110, the wavelength button 112, the flag value button 114, the intensity button 116, and the Group ID button 118.

Figure 3:
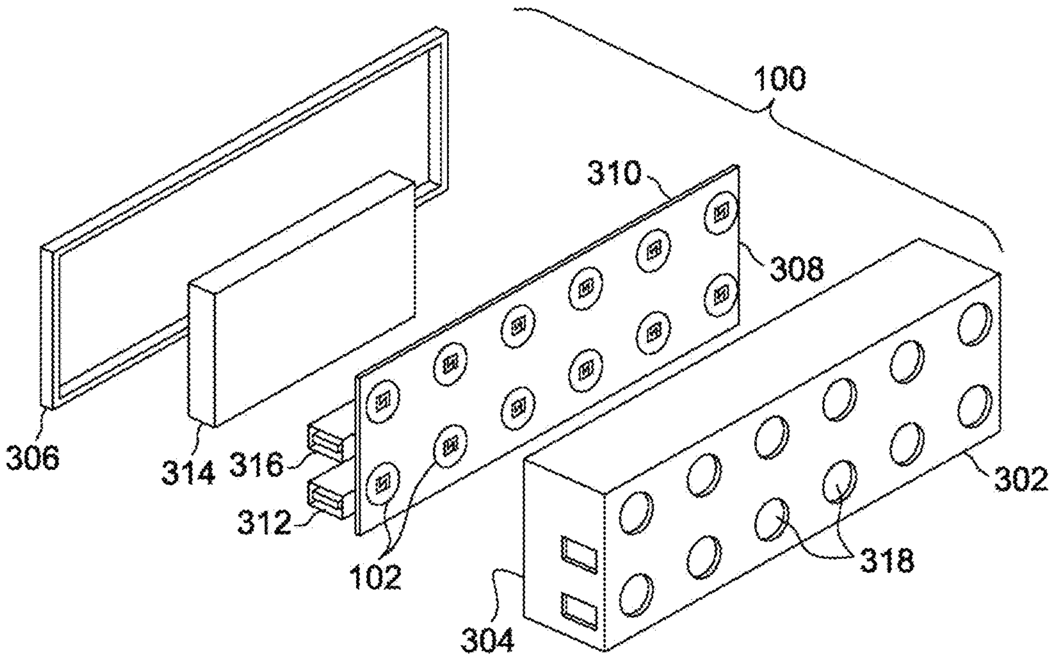
FIG. 3 shows an exploded view of a lighting panel in accordance with an embodiment of the present invention.

FIG. 3 shows an exploded view of a lighting panel in accordance with an embodiment of the present invention. The lighting panel 100 comprises a top cover 302 having a housing 304, and a bottom cover 306. The housing provides a space for accommodating a plate 308 comprising a plurality of LEDs 102. The plurality of LEDs 102 are arranged in an array on the plate 308. The bottom of the plate 308 is provided with a circuit board 310 comprising a PCB for controlling or regulating the plurality of LEDs 102 by receiving inputs from the control unit 104. The control unit 104 comprises a user interface 106 and a plurality of buttons to control one or more parameters for regulating the lighting effect of the plurality of LEDs 102. The circuit board also comprises a connection interface for connecting with a network of other lighting panels and with an external communication device. The circuit board 310 is connected to a power source which can be a battery 314. A charging interface 316 is provided on the circuit board to charge the battery 314. The top cover 302 is provided with a plurality of holes 318 with a transparent surface to allow the light emitted from the plurality of LEDs 102 to pass through. The top cover 302 is connected with the bottom cover 306 to enclose the plate 308 having plurality of LEDs, the control unit 104, and the battery 314.

Figure 4:
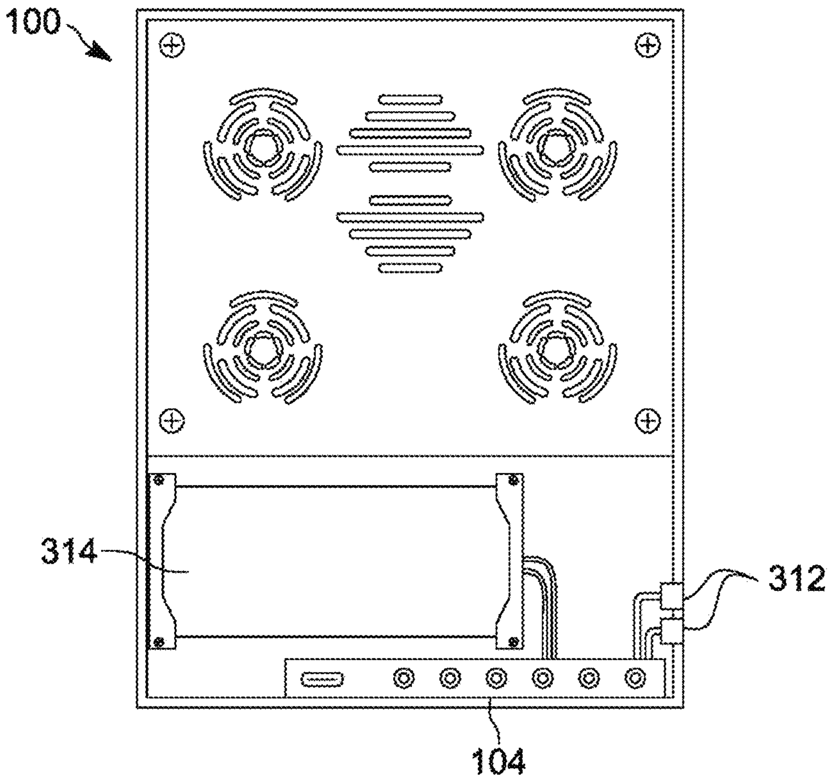
FIG. 4 illustrates a back view of the lighting panel 100 in accordance with an embodiment of the present invention.

FIG. 4 illustrates a back view of the lighting panel 100 in accordance with an embodiment of the present invention. The lighting panel 100 has the control unit 104 with a plurality of buttons to regulate one or more control parameters for operating the plurality of LEDs 102. The connection interface 312 comprises either a port for providing wired connectivity to the network or a wireless network interface for providing wireless connectivity to the lighting panel 100. The battery 314 is connected to the control unit 104 and the plurality of LEDs 102. The charging interface 316 is provided in the lighting panel 100 to charge the battery.

In an embodiment of the present invention, the one or more control parameters that can be set by the plurality of buttons include light intensity, type selection (therapeutic, examination light, standard mode, intensive mode), intensity of light, wavelength, mode (continuous, pulsed, intermittent), time duration or operating time, power density or energy density, color temperature, light distribution, dimming, etc. The user can use the control unit to set or update the one or more control parameters. When a change is made in any of the control parameters, a flag value corresponding to the timestamp at which the control parameter is updated for the lighting panel is generated by the control unit.

In an embodiment of the present invention, the connection interface 312 provides wireless or wired connectivity to the lighting panel 100 with other lighting panels or with an external device. The wired connection interface includes but is not limited to LAN, WAN, HDMI, USB. The wireless connection interface comprises but is not limited to a Bluetooth protocol, ZIGBEE, mesh network, Wi-Fi, cellular, Infrared, NFC, Z-wave, BLE, and wireless ad hoc network.

The lighting panel 100 transmits the flag value along with the current control parameters for the lighting panel to other lighting panels in the network. The lighting panel 100 also receives the current control parameters of each of the other lighting panels in the network along with their corresponding flag values. The control unit 104 compares the flag value of the lighting panel with the flag values received from other lighting panels in the network to determine the highest flag value. The control unit identifies the highest flag value and copies the control parameters associated with the highest flag value and propagates the copied control parameters. The control unit updates the control parameters of the highest flag value into the lighting panel, such that the lighting panel 100 now operates with the control parameters of that lighting panel in the network which has the highest flag value, i.e. control parameters of the lighting panel in which the control parameters has been changed recently.

In an embodiment of the present invention, the flag value in a lighting panel can be changed manually using the control unit 104. The control unit 104 is provided with a flag value button 114 through which the user can update the flag value such that the lighting panel has a recent flag value. When the lighting panel 100 transmits the flag value along with the one or more control parameters, the flag value being the recent has the highest value, therefore, other lighting panels in the network copy the control parameters of the lighting panel 100 and update their control parameters with the control parameter of the lighting panel 100.

In an embodiment of the present invention, the plurality of LEDs 102 of the lighting panel 100 can be controlled to operate with a plurality of control parameters. The control unit 104 is configured to change each of the plurality of control parameters for the operation of LEDs 102. Each of the plurality of control parameters is associated with a corresponding flag value. When any of the control parameters is updated by the user, the change is associated with the corresponding flag value. If the lighting panel 100 is configured to operate with n parameters, then for each of the n parameters, n flag values can be generated. When the lighting panel 100 transmits and receives the data packet in the network, the control unit 104 identifies the highest corresponding flag value for each of the control parameters and updates the corresponding control parameter having the highest flag value.

In an embodiment of the present invention, the lighting panel 100 is assigned with a Group ID. The lighting panel 100 transmits the information of Group ID to other lighting panels in the network. The data packet transmitted and received by the lighting panel 100 in the network contains information on Group ID, Flag value, and one or more control parameters for operating the plurality of LEDs 102. When the lighting panel 100 receives data from other lighting panels in the network, the control unit 104 compares the Group ID of the data packet with the Group ID of the lighting panel 100. If the Group ID of the received data packet is the same as that of Group ID of the lighting panel 100, the control unit 104 then compares the flag value of the data packet with the flag value of the lighting panel and adopts the one or more control parameter associated with the highest flag value.

In an embodiment of the present invention, the lighting panel 100 is inherently provided with the Group ID, or the control unit 104 is configured to update the Group ID. When a lighting panel is powered on after being turned off, the lighting panel initializes in default mode. During network setup, the user assigns a Group ID to the lighting panel, enabling it to establish a connection with other lighting panels sharing the same Group ID. Upon connection, all lighting panels in the network start with their default control parameter settings. For instance, If a first lighting panel is operating with a first control parameter having a first value and a second control parameter with a second value is connected in a network with a second lighting panel operating with the first control parameter and the second control parameter with a value different than the first lighting panel, then upon connection, both the first lighting panel and the second lighting panel initializes with default values of the first control parameter and the second control parameter.

In an embodiment of the present invention, the lighting panel further comprises one or more sensors for monitoring ambient conditions, parameters of a target surface and the internal parameters of the lighting panel. The control unit communicates the data collected by the sensor and communicates the data to other lighting panels in a network. The sensor data can be communicated to an external communication device connected with the network of plurality of lighting panel. Based on the feedback on the ambient condition, the user can modify the control parameters of the lighting panel using the external communication device, such as a smartphone or a mobile device. The one or more control parameters can be changed in the lighting panel based on the feedback received from the one or more sensors.

Figure 5:
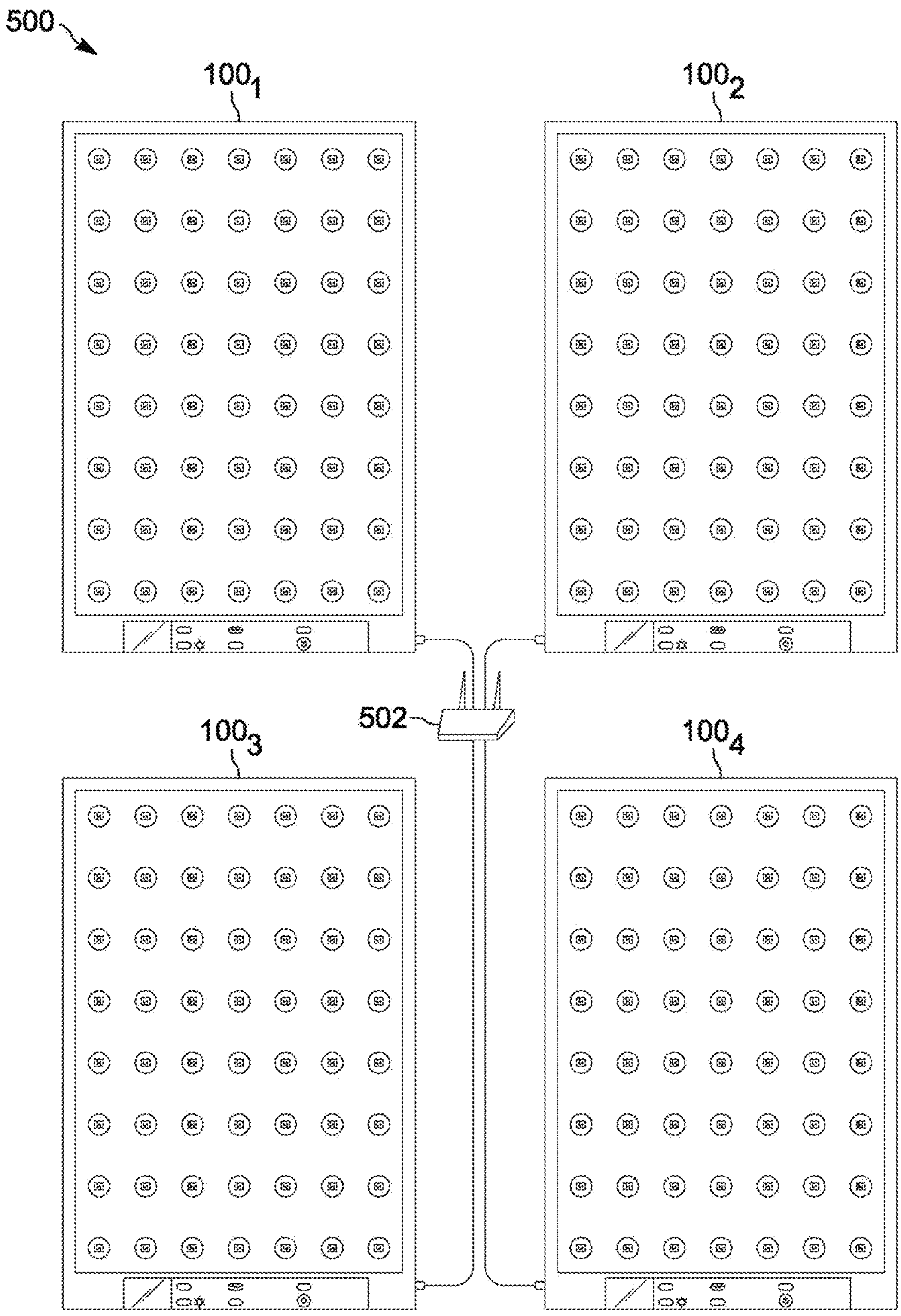
FIG. 5 illustrates a system comprising a plurality of lighting panels in a network using wired connectivity.

FIG. 5 illustrates a system 500 comprising a plurality of lighting panels (1001, 1002, 1003, 1004) in a network using wired connectivity. Each of the plurality of lighting panels ($100_1$, $100_2$, $100_3$, $100_4$) are connected with each other using a wired connection 502. Each of the plurality of lighting panels ($100_1$, $100_2$, $100_3$, $100_4$) has a control unit to update one or more control parameters for operating the LEDs 102. When a user updates any of the one or more control parameters, the flag value corresponding to the time stamp is generated and communicated to other lighting panels in the network. The transmission of data packets containing flag value and the one or more control parameters is continuous or at regular intervals in the network. Each of the plurality of lighting panels ($100_1$, $100_2$, $100_3$, $100_4$) receives the flag value and corresponding control parameters of other lighting panels in the network and identifies the highest flag value. Each of the lighting panels then updates the one or more control parameters corresponding to the highest flag value and accordingly adjusts the parameters for illumination for the plurality of LEDs. For example, if a user made any changes in the one or more control parameters of the plurality of LEDs for the lighting panel $100_4$, the updated parameters are generated with the recent flag value. The lighting panel $100_4$ being in communication with other lighting panels transmits the updated flag values along with the one or more control parameters in the network to other lighting panels ($100_1$, $100_2$, $100_3$). The other lighting panels ($100_1$, $100_2$, $100_3$) compare the flag value of lighting panel $100_4$ with the respective flag value. Once the other lighting panels ($100_1$, $100_2$, $100_3$) identify the flag value of the lighting panel $100_4$ being the latest, each of the other lighting panel updates the respective one or more control parameters to illuminate the plurality of LEDs with updated control parameters.

In an embodiment, in the system, each of the plurality of the lighting panels ($100_1$, $100_2$, $100_3$, $100_4$) is assigned a Group ID. Each of the plurality of the lighting panels ($100_1$, $100_2$, $100_3$, $100_4$) transmits the information of Group ID to other lighting panels in the network. The data packet transmitted and received by each of the lighting panels in the network contains information on Group ID, Flag value, and one or more control parameters for operating the plurality of LEDs. When the lighting panel receives data from other lighting panels in the network, the control unit compares the Group ID of the data packet with the Group ID of the lighting panel. If the Group ID of the received data packet is the same as that of the Group ID of the lighting panel, the control unit then compares the flag value of the data packet with the flag value of the lighting panel and adopts the one or more control parameter associated with the highest flag value.

In an embodiment of the present invention, the one or more control parameters that can be set by the plurality of buttons include light intensity, type selection (therapeutic, examination light, standard mode, intensive mode), intensity of light, wavelength, frequency, mode (continuous, pulsed, intermittent), time duration or operating time, duty cycle, dosage, rate of emission, power density or energy density, color temperature, light distribution, dimming, etc.

In an embodiment of the present invention, the plurality of LEDs 102 of the plurality of lighting panels ($100_1$, $100_2$, $100_3$, $100_4$) can be controlled to operate with a plurality of control parameters. The control unit 104 in each of the plurality of lighting panels ($100_1$, $100_2$, $100_3$, $100_4$) is configured to change any of the control parameters for the operation of LEDs 102. Each of the plurality of control parameters is associated with a corresponding flag value. When any of the control parameters are updated by the user, the change is associated with the corresponding flag value. If the lighting panel 100 is configured to operate with n parameters, then for each of the n parameters, n flag values can be generated. If a first control parameter is changed for the lighting panel $100_1$ and a second control parameter is changed for the lighting panel $100_2$ and a third control parameter is changed for the lighting panel $100_3$, then for the first control parameter a first flag value is updated by the lighting panel $100_1$, for the second control parameter, a second flag value is updated by the lighting panel $100_2$, and for the third control parameter, a third flag value is updated by the lighting panel $100_3$. Each of the plurality of lighting panels ($100_1$, $100_2$, $100_3$, $100_4$) in the network transmits and receives data packets from other lighting panels in the network. When the lighting panel $100_1$ receives the data packet from other lighting panels, the control unit compares the flag value for the first control parameter, the second control parameter, and the third control parameter with the flag value of its own. In this case, the lighting panel $100_1$ finds the first flag value of its own as the latest updated and retains the first control parameter as such, while the second flag value is highest for the lighting panel $100_2$ and the third flag value is highest for the lighting panel $100_3$, therefore the first lighting panel will update the second control parameters with the second control parameter of the lighting panel $100_2$, and update the third control parameter with the corresponding third parameter of the lighting panel $100_3$. Similarly, the lighting panel $100_2$ updates the first control parameter with the corresponding first parameter of the lighting panel $100_1$ and the third control parameter with the corresponding third parameter of the lighting panel $100_3$. Similarly, the lighting panel $100_3$ updates the first control parameter with the corresponding first parameter of the lighting panel $100_1$ and the second control parameter with the corresponding second parameter of the lighting panel $100_2$. Similarly, the lighting panel $100_4$ updates the first control parameter with the corresponding first parameter of the lighting panel $100_1$, the second control parameter with the corresponding second parameter of the lighting panel $100_2$, and the third control parameter with the corresponding third parameter of the lighting panel $100_3$.

In an embodiment of the present invention, the lighting panel further comprises one or more sensors for monitoring ambient conditions, parameters of a target surface and the internal parameters of the lighting panel. The control unit communicates the data collected by the sensor and communicates the data to other lighting panels in a network. The ambient conditions include lighting parameters, temperature, occupancy etc. The parameter of the target surface include the intensity of light falling on the target surface, and exposure of the target surface. The internal parameters of the lighting panel include temperature and other physical parameters of the lighting panel. Based on the feedback from sensor, one or more control parameters in the lighting panel can be updated in the lighting panel or through the external communication device by the user.

Figure 6:
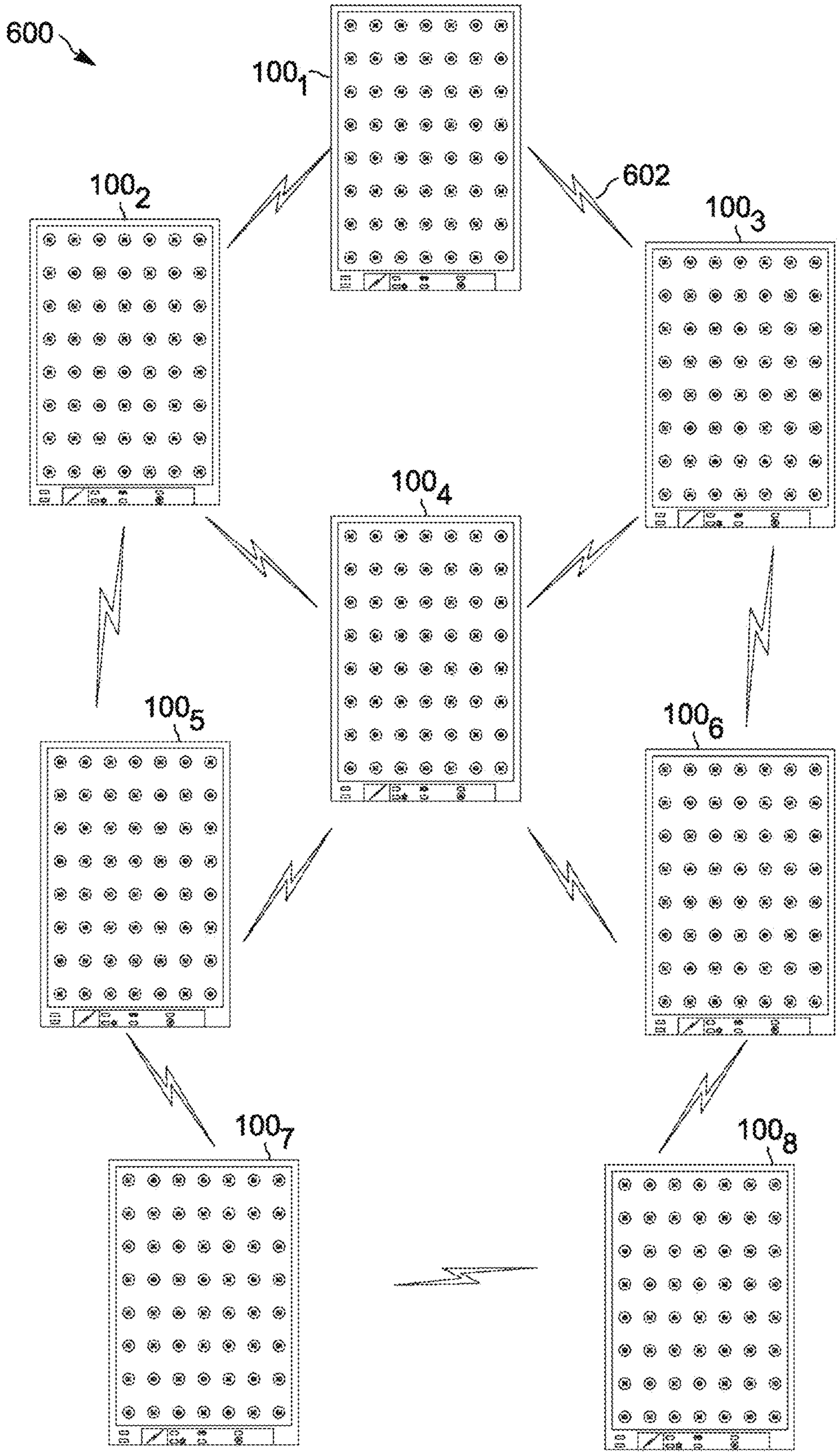
FIG. 6 illustrates a system for controlling the plurality of controlling the plurality of lighting panels in a wireless network in accordance with an embodiment of the present invention.

FIG. 6 illustrates a system 600 for controlling the plurality of controlling the plurality of lighting panels in a wireless network, such as Bluetooth. In FIG. 6, a plurality of lighting panels ($100_1$, $100_2$, $100_3$, $100_4$, $100_5$, $100_6$, $100_7$, $100_8$) are connected through Bluetooth/BLE network. The wireless network works like a MESH network, in which each of the plurality of lighting panels ($100_1$, $100_2$, $100_3$, $100_4$, $100_5$, $100_6$, $100_7$, $100_8$) are placed within the same network and operate as a node, wherein each node can both receive and transmit information. Each of the plurality of lighting panels ($100_1$, $100_2$, $100_3$, $100_4$, $100_5$, $100_6$, $100_7$, $100_8$) acting as a node had a wireless transmission range and some of the lighting panels are out of reach from other nodes. For Example, the lighting panel $100_1$ is within reach of the lighting panels ($100_2$, $100_3$), and lighting panels ($100_4$, $100_5$) are within reach of the lighting panel $100_2$, and the lighting panels ($100_4$, $100_6$) are within reach of the lighting panel $100_3$. Because of the MESH network, the lighting panel $100_1$ transmits and receives information from the lighting panel $100_2$, which in turn transmits and receives information from the lighting panel $100_5$. In this way, the connection between the lighting panel $100_1$ and the lighting panel $100_5$ is realized. In this manner, in the Bluetooth wireless network, each of the plurality of lighting panels ($100_1$, $100_2$, $100_3$, $100_4$, $100_5$, $100_6$, $100_7$, $100_8$) are in communication with the other lighting panels.

When a user updates one or more control parameters in any of the plurality of control parameters for operating the plurality of LEDs (light source) in any of the plurality of lighting panels ($100_1$, $100_2$, $100_3$, $100_4$, $100_5$, $100_6$, $100_7$, $100_8$), the updation in one or more control parameters gets associated with a flag value. The update flag value with the corresponding one or more control parameters is transmitted through the wireless network through the nodes (the plurality of lighting panels). Each of the plurality of lighting panels ($100_1$, $100_2$, $100_3$, $100_4$, $100_5$, $100_6$, $100_7$, $100_8$) compares the flag value received through other nodes and updates the one or more control parameters with the corresponding highest flag value.

In an embodiment of the present invention, each of the plurality of the control parameter is associated with a flag value, such that change in the first control parameter is associated with the first flag value, change in the second control parameter is associated with the second flag value, and like. Each lighting panel in the network compares each flag value corresponding to each control parameter and updates each of the control parameters having the highest corresponding flag value.

In an embodiment of the present invention, each of the plurality of lighting panels ($100_1$, $100_2$, $100_3$, $100_4$, $100_5$, $100_6$, $100_7$, $100_8$) in the Bluetooth network are assigned with a Group ID, such that lighting panels with the same Group ID is a member of a same group. The communication between the nodes in the network is through the MESH network, wherein each lighting panel will act as a node to transmit information received from other nodes in the network. However, the lighting panel will compare the flag values for the control parameters that have a group ID the same as that of the lighting panel. Therefore, the members of the same group compare the flag value to update changes in the control parameters.

Figure 7:
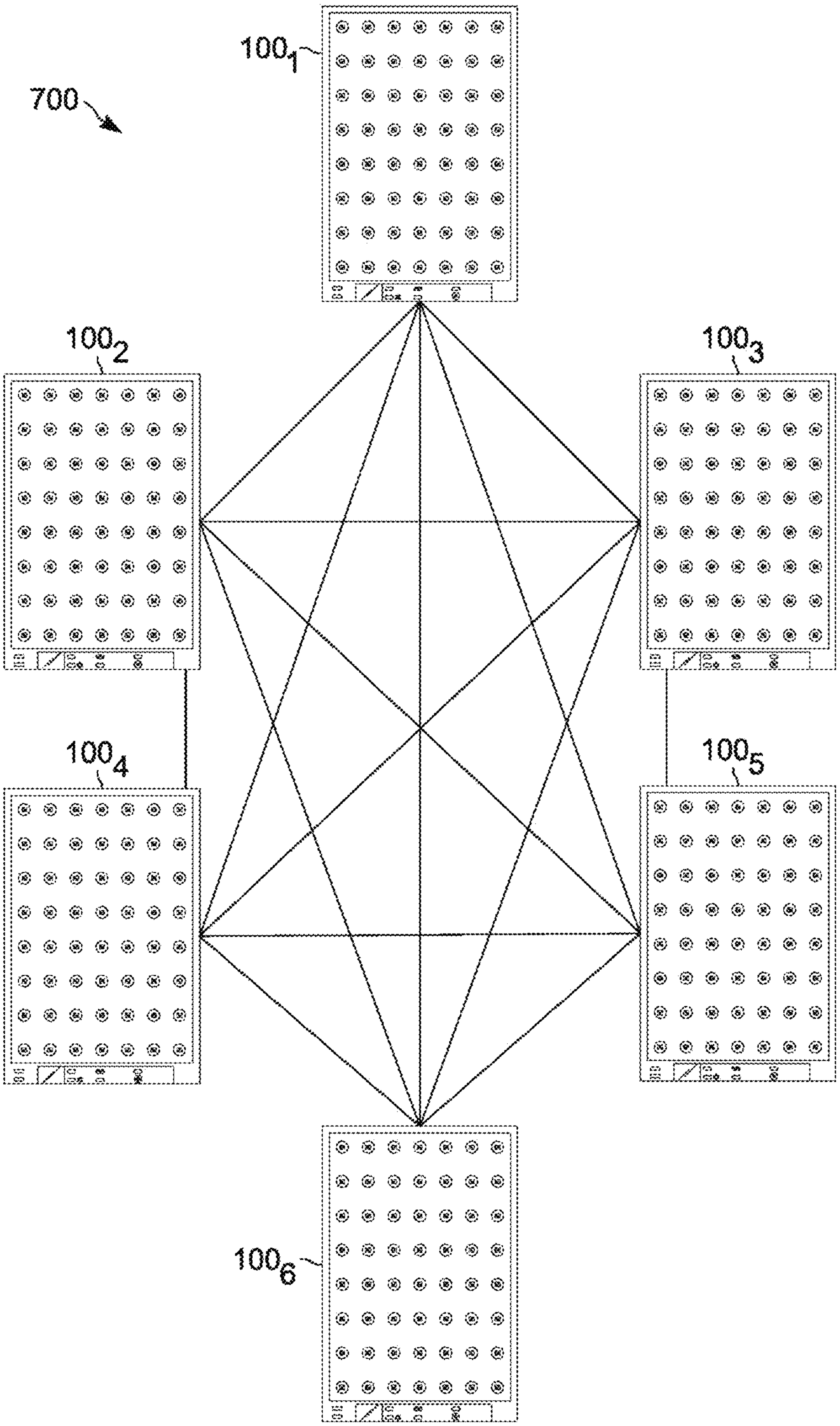
FIG. 7 illustrates a lighting panel control system in a wireless network, where each of the lighting panels is in communication with other lighting panels through the wireless network in accordance with an embodiment of the present invention.

FIG. 7 illustrates a lighting panel control system 700 in a wireless network, where each of the lighting panels is communicated to other lighting panels through the wireless network. As shown in FIG. 7, each of the plurality of lighting panels ($100_1$, $100_2$, $100_3$, $100_4$, $100_5$, $100_6$) is in communication with other lighting panels through the wireless network. The communication is either through a router or through a wireless communication device. The one or more control parameters of each of the lighting panels ($100_1$, $100_2$, $100_3$, $100_4$, $100_5$, $100_6$) are updated by comparing flag values associated with the one or more control parameters. Each of the control parameters can be associated with a corresponding flag value. The plurality of lighting panels ($100_1$, $100_2$, $100_3$, $100_4$, $100_5$, $100_6$) can be assigned with a Group Id so that the lighting panels with the same Group ID are a member of the same group. The flag values are read for the members falling within the same group.

Figure 8:
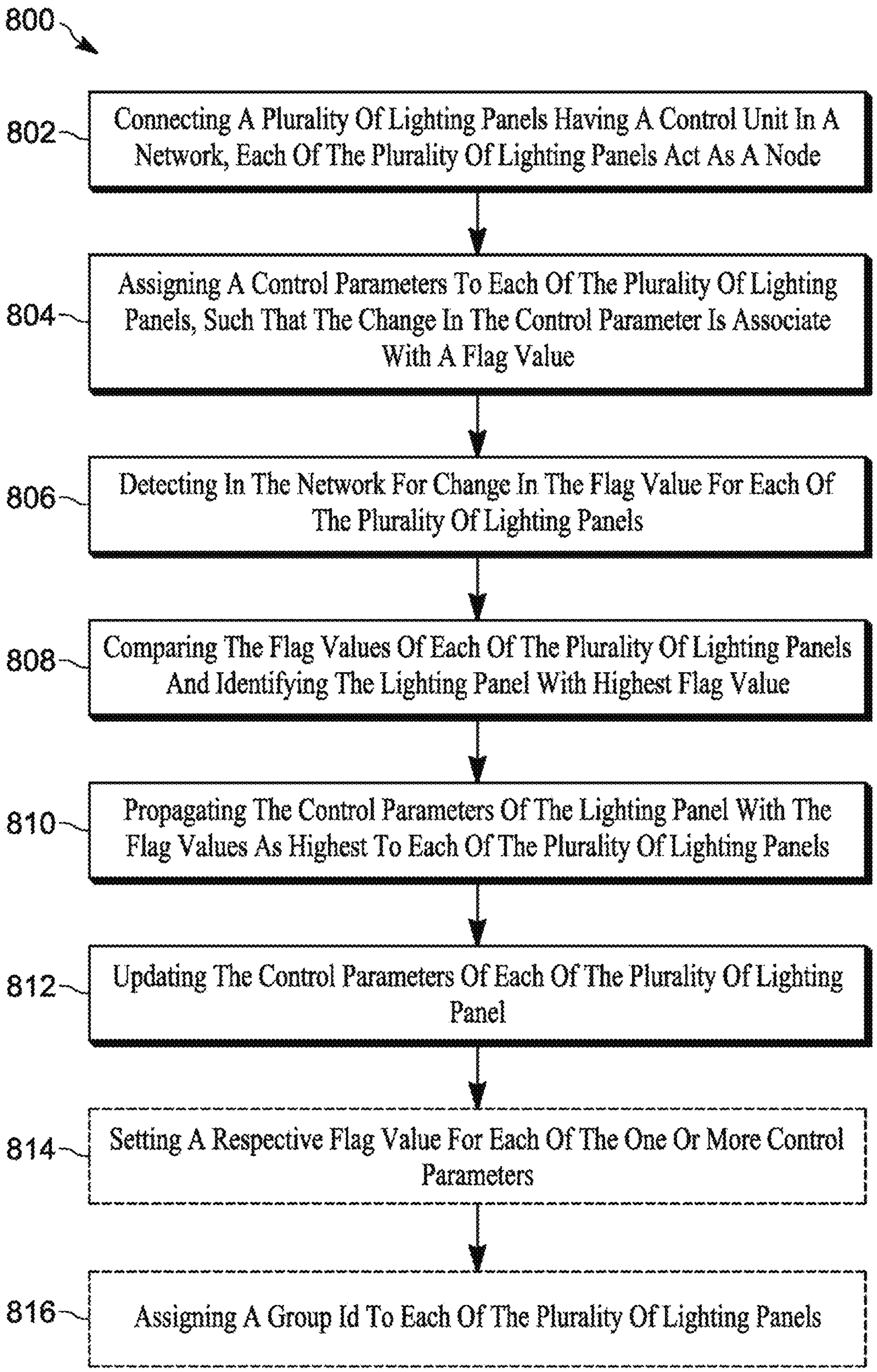
FIG. 8 illustrates a method for controlling a lighting system in accordance with an embodiment of the present invention.

FIG. 8 illustrates a method 800 for controlling a lighting system in accordance with an embodiment of the present invention. In step 802, a plurality of lighting panels are connected in a network. The network can be a wired network or a wireless network, such as Bluetooth, or mesh network. Each of the plurality of lighting panels comprises a control unit and acts as a node in the network. In step 804, each of the plurality of lighting panels is assigned with a set of control parameters, such that the timestamp of any change in the set of control parameters is noted as a Flag value. In step 806, the plurality of lighting panels detects for any change in the flag value of the data packets that are received over the network. In step 808, each of the plurality of lighting panels compares the flag value for the set of control parameters in the data packets received over the network and the flag value in the lighting panel and identifies the lighting panel with the highest flag value for the set of control parameters. In step 810, the set of control parameters associated with the identified highest flag value is propagated in the network to the plurality of lighting panels. In step 812, the set of control parameters associated with the highest flag value is implemented in each of the plurality of lighting panels.

In an embodiment of the present invention, if a lighting panel comprises a plurality of control parameters for operating the plurality of LEDs, then each control parameter is assigned a respective flag value (Step 814). Each of the plurality of lighting panels in the network compares the flag value for each of the control parameters and updates particular control parameters with the highest flag value in the lighting panel.

In an embodiment of the present invention, the method further comprises assigning a Group ID to each of the plurality of lighting panels (Step 816). The lighting panels with the same group ID are considered as member of the same group. When a lighting panel receives the data packet of other lighting panels, the lighting panel first identifies whether the other panel is a member of the same group. The control parameters are updated only when the flag value is highest among the members of the same group.

Figure 9A:
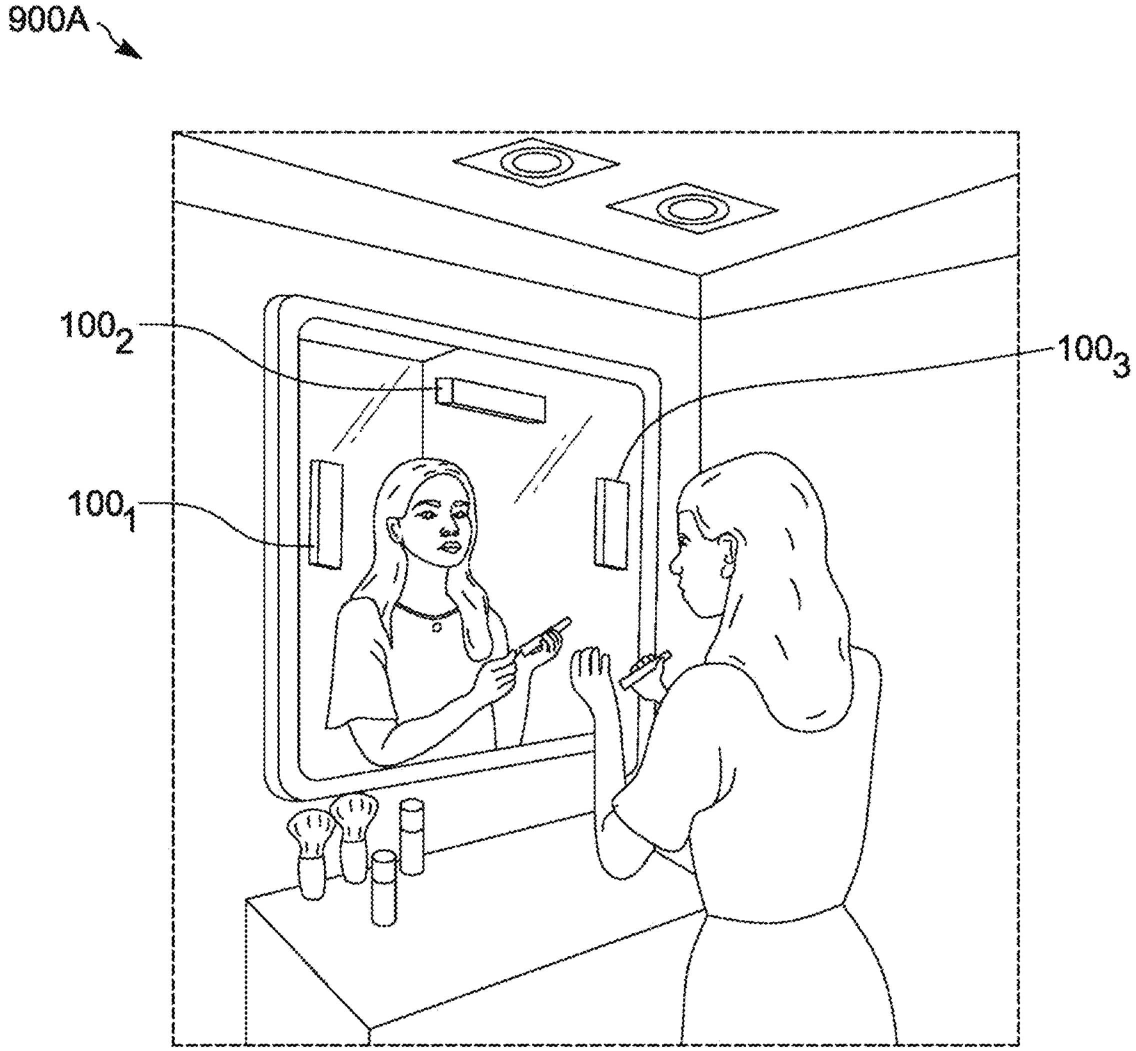
FIG. 9A illustrates the application of a lighting panel control system in a personal lighting system in accordance with an exemplary embodiment of the present invention.

FIG. 9A illustrates the application of the lighting panel control system in personal lighting systems in accordance with an exemplary embodiment of the present invention. The personal lighting system 900A is generally a plurality of portable lighting panels ($100_1$, $100_2$, $100_3$) that a user can use to provide illumination in studios or make-up rooms. FIG. 9A shows a user using a plurality of lighting panels on a mirror in a make-up room. By using the lighting panel control system, the user can update the illumination level or intensity in one of the lighting panels, and the change in control parameter with the corresponding flag value is communicated to other lighting panels in the network. The other lighting panel identifies the illumination level or intensity in a particular lighting panel having the highest flag value and copies the corresponding intensity level in other lighting panels. The other lighting panel then adjusts the illumination level or intensity to the level of the lighting panel in which changes have been made. The lighting panel control panel thus eliminates the need for the user to change the illumination level in each of the plurality of lighting panels, thus easing the user's comfort.

Figure 9B:
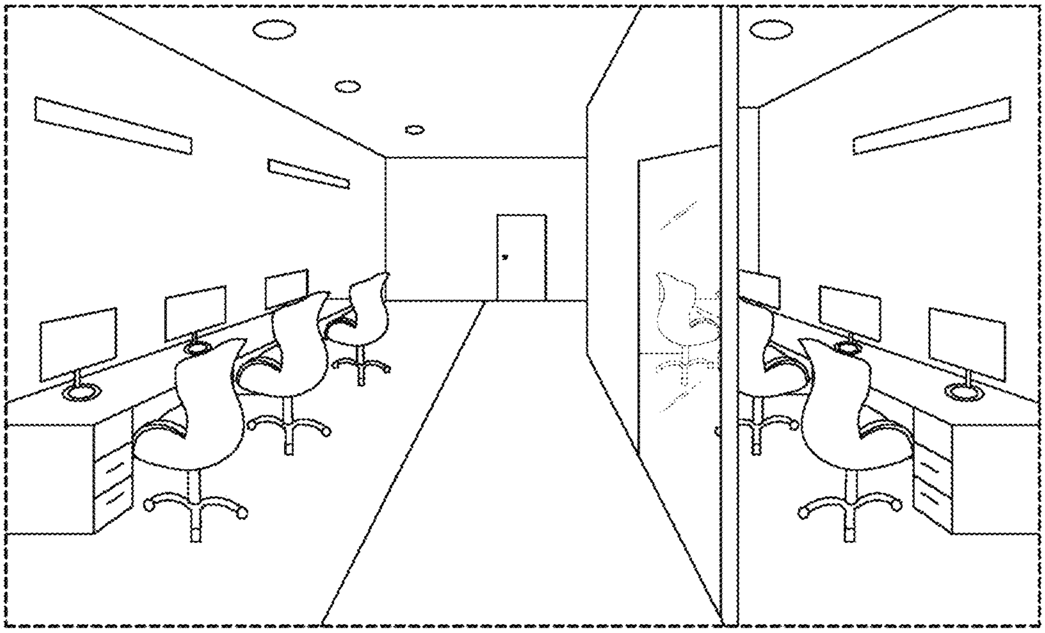
FIG. 9B illustrates the use of the lighting control system in an office space in accordance with an exemplary embodiment of the present invention.

FIG. 9B illustrates the use of the lighting control system in an office space in accordance with an exemplary embodiment of the present invention. In an office or commercial building, the requirement for lighting may vary from one space to another. FIG. 9B shows a plurality of lighting panels installed in an office space 900B. The lighting panel installed in one space is assigned with the same Group ID, so that a change made in one lighting panel is propagated to all other lighting panels installed in the particular space. This eliminates the need to control each lighting panel individually. Further, if a change needs to be made in a particular area, then the same Group ID can be assigned to the lighting panels installed in that area, so that even if a change in lighting parameter is made in one of the lighting panels, it will not affect the lighting panel installed in other areas.

Figure 9C:
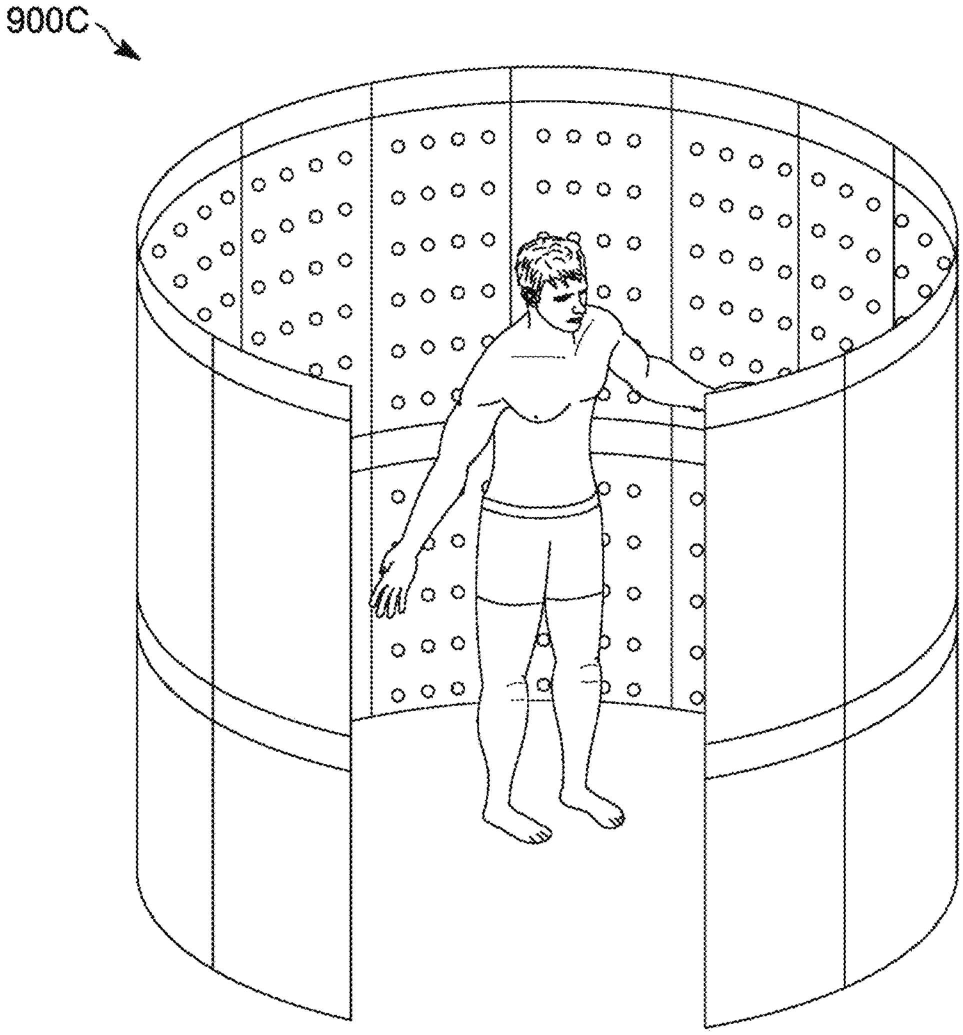
FIG. 9C illustrates the application of the lighting control system in a phototherapy technique in accordance with an exemplary embodiment of the present invention.

FIG. 9C illustrates the application of the lighting control system in a phototherapy technique in accordance with an exemplary embodiment of the present invention. In the phototherapy technique 900C, different parts of a user are irradiated with lights with varying wavelengths, and intensity. Furthermore, treatment processes are designed for performing certain LED panels to emit light for different time durations. In FIG. 9C, the lighting panels are assigned in a plurality of Group ID so as to form the same group for those lighting panels that need to function in a synchronous manner. The time duration can be set for the same group member by setting the time duration in one of the lighting panels belonging to that group. Similarly, intensity and wavelength are defined for different groups and can be updated by making a change in a single lighting panel belonging to the same group, which is then propagated to other lighting panels of the same group.

Figure 9D:
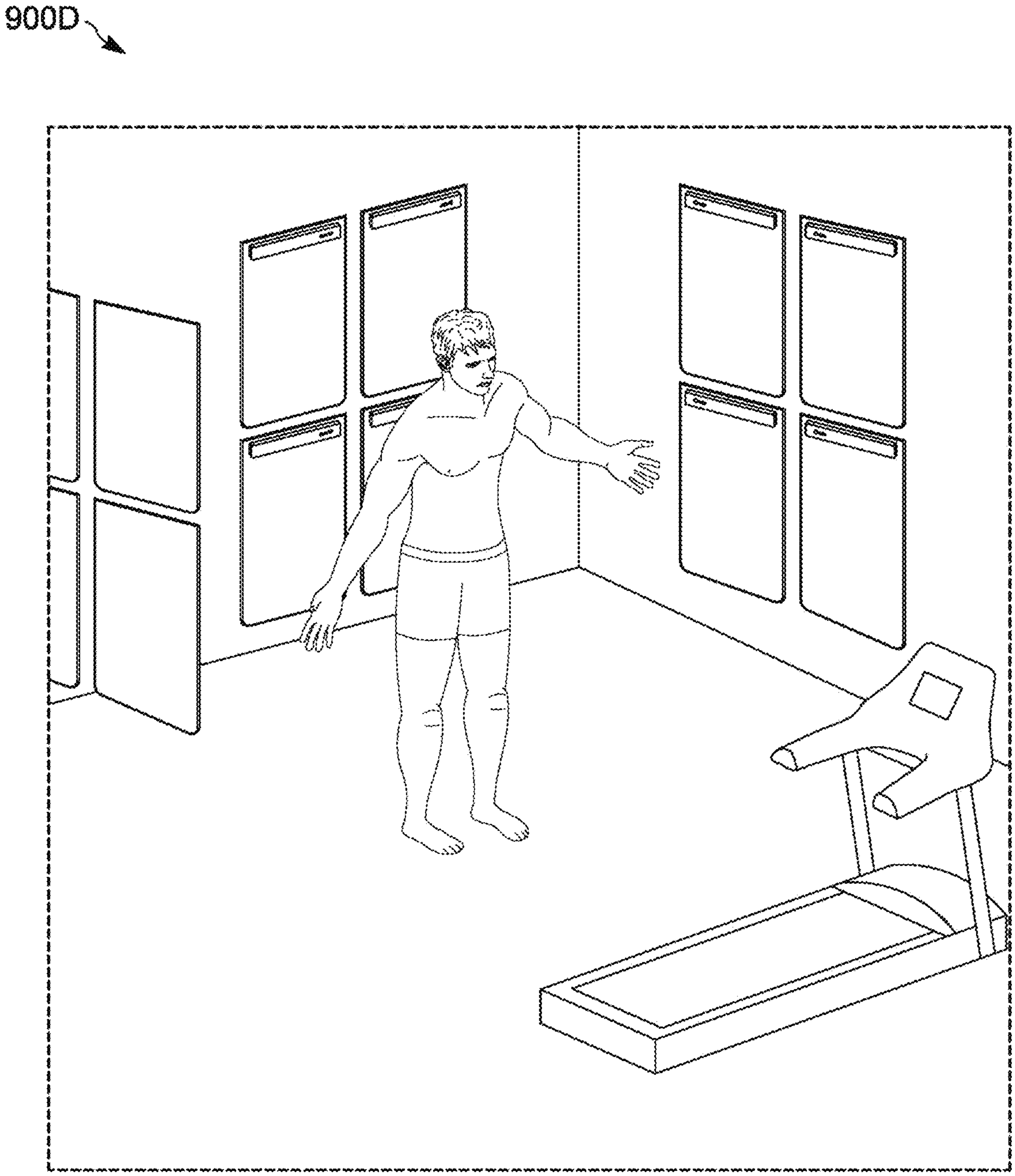
FIG. 9D illustrates the application of the lighting control system in a fitness center in accordance with an exemplary embodiment of the present invention.

FIG. 9D illustrates the application of the lighting control system in a fitness center in accordance with an exemplary embodiment of the present invention. The lighting panels in the fitness center 900D are connected through the wireless network. If a user wish to make a change in the intensity or illumination level in the lighting device installed in a corresponding segment of the fitness center, then the user can make a change in one of the lighting panels which is then propagated to other lighting panels.

The system and method of the present invention provides various advantages. The control system described in the present invention is decentralized, wherein the control parameters for all the lighting panels in the network or the lighting panels forming a same group can be controlled by updating the control parameter in any of the lighting panel. This is particularly advantageous over the centralized control structure, where a master device controls the updation of the control parameters of associated slave device.

The logic for the updation of control parameters is based on Flag-based and autonomous rather than master initiated and global for all the lighting panels in the network. The communication between the lighting panel is bidirectional, where each of the lighting panel transmits and receives the information to other lighting panels in the network. In the centralized control system, the communication is predominately unidirectional, where the master device communicates the control parameters to the slave device and each of the slave devices follows the control parameter as updated in the master device.

Another advantage of the control system of the present invention is that being decentralized, wherein each lighting panel transmits and receives the control parameters of other lighting panel in the device, and the updation of control parameters values are based on the flag value, there is no single point of failure. In a centralized control system, if a master device malfunctioned, the updation logic fails for all the connected devices in the system.

Furthermore, the control system of the present invention is dynamic and flexible, wherein each lighting panel acts as a controller for updating the control parameters. Whereas in the conventional centralized control system, the logic is rigid and requires setting of master and slave configuration.

The control system of the present invention provides dual control capability. Each of the control parameters may be associated with a separate flag value and all the lighting panels in the network transmits or receives the information on flag value and control parameters. F one control parameter is updated in one lighting panel and other control parameter is updated in other lighting panel, then all the lighting panels in the network update the control parameters of the latest value. Therefore, a lighting panel can control some parameters while other parameters are regulated based on updation in other lighting panels. Whereas in conventional centralized control system, the control is fixed, wherein the master device controls and slave device executes.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to provide the broadest scope consistent with the principles and the novel and inventive features disclosed or suggested herein. Accordingly, the invention is anticipated to hold on to all other such alternatives, modifications, and variations that fall within the scope of the present invention.

The invention claimed is:

1. A lighting panel comprising:
one or more light sources;
a control unit, configured to:
allow a user to set one or more control parameters for the lighting panel;
update a Flag value associated with the lighting panel;
a connection interface, configured to:
enable the lighting panel to communicate with a plurality of other lighting panels within a network;
transmit and receive data corresponding to the Flag value and the one or more control parameters among the plurality of other lighting panels;
wherein the control unit is further configured to:
compare the Flag value of the lighting panel with a Flag value received from each of the plurality of other lighting panels;
identify a highest Flag value lighting panel among the plurality of other lighting panels; and
adopt the one or more control parameters associated with the highest Flag value lighting panel.

2. The lighting panel of claim 1, wherein the control unit is further configured to: update the Flag value manually by receiving an input from the user, or update the Flag value automatically when the one or more control parameters are modified for the lighting panel.

3. The lighting panel of claim 1, wherein each of the one or more control parameters of the lighting panel is associated with a corresponding Flag value; and
the control unit is configured to update the corresponding Flag value in response to a modification of the associated control parameter for the lighting panel.

4. The lighting panel of any of claim 1, wherein the control unit allows a user to set a Group ID for the lighting panel and the connection interface is configured to transceive data corresponding to the Group ID, the Flag value and the one or more control parameters for the lighting panel.

5. The lighting panel of any of claim 1, wherein the control unit is configured to compare the Flag value of the lighting panel and the Flag value received from each of the plurality of other lighting panels having the Group ID same as of the Group ID of the lighting panel, identify a highest Flag value lighting panel and adopts the one or more control parameters associated with the highest Flag value lighting panel.

6. The lighting panel of claim 1, wherein the one or more light sources comprises therapeutic light source.

7. The lighting panel of claim 1, wherein the lighting panel is configured to connect with an external device to monitor and update the one or more control parameters of the lighting panel.

8. The lighting panel of claim 1, wherein the lighting panel further comprises one or more sensors for monitoring parameters of a target surface, and the lighting panel, and the control unit communicate the ambient conditions to the plurality of other lighting panels in the network.

9. A lighting panel control system comprising:
a network of a plurality of lighting panels, each of the plurality of lighting panels comprising:
one or more light sources;
a control unit configured to assign a Flag Value and allow a user to set a one or more control parameters for the lighting panel;

a connection interface that enables each of the plurality of lighting panels to connect with each other to transceive data corresponding to the Flag value and the one or more control parameters for the lighting panel;

wherein each of the plurality of lighting panels acts as a node in the network; and wherein each of the plurality of lighting panels compares the Flag value for the plurality of lighting panels to identify a highest Flag value lighting panel and adopts the one or more control parameters associated with the highest Flag value lighting panel.

10. The lighting panel of claim 9, wherein the control unit is further configured to: assign the Flag value manually by receiving an input from the user, or assign the Flag value when the one or more control parameters are modified for a lighting panel.

11. The lighting panel of claim 9, wherein each of the one or more control parameters for the lighting panel is associated with a corresponding Flag value; and the control unit is configured to update the corresponding Flag value in response to a modification of the associated control parameter for corresponding lighting panel.

12. The lighting panel of claim 9, wherein the control panel allows a user to set a Group ID for the lighting panel, and the connection interface transceive data corresponding to the Group ID, the Flag value and the one or more control parameters for the lighting panel.

13. The lighting panel of claim 9, wherein the control unit compares the Flag value of the lighting panel and the Flag value received from each of the plurality of other lighting panels having the Group ID same as of the Group ID of the lighting panel, identify a highest Flag value lighting panel and adopts the one or more control parameters associated with the highest Flag value lighting panel.

14. A lighting panel control system comprising:

a network of a plurality of lighting panels to exchange data between each of the plurality of lighting panels;

wherein each of the plurality of lighting panels comprises:

a connection interface to connect with each of the plurality of lighting panels in the network;

a control unit that allows a user to set a Group ID, and one or more control parameters for the lighting panel, wherein each of the one or more control parameters is associated with a corresponding Flag value;

wherein each of the plurality of lighting panels acts as a node in the network and each of the plurality of lighting panels with a value of the Group ID same are identified as a member of a same group; and wherein the control unit in each of the plurality of lighting panels is configured to:

monitor the Flag value corresponding to each of the one or more control parameters of the members of the same group;

identify, for each of the one or more control parameters, a highest Flag value member; and adopt each of the one or more control parameters associated with the highest Flag value member.

15. The lighting panel control system of claim 14, wherein the one or more control parameters comprises intensity, wavelength, frequency, duty cycle, pulse width, power, duration, dosage, rate of emission, and mode.

16. The lighting panel control system of claim 14, wherein one of the one or more control parameters is intensity of light, and is associated with a first Flag value such that each of the plurality of lighting panels monitor for a highest first Flag value and update the intensity of light for each of the plurality of lighting panels corresponding to value of one or more control parameter with the highest first Flag value.

17. The lighting panel control system of claim 14, wherein one of the one or more control parameter is wavelength of light, and is associated with a second Flag value such that each of the plurality of lighting panels monitor for a highest second Flag value and update wavelength of light for each of the plurality of lighting panel corresponding to value of one or more control parameter with the highest second Flag value.

18. A method for controlling a plurality of lighting panels in a network, the method comprising:

connecting the plurality of lighting panels in the network wherein each of the plurality of lighting panels acts as a node in the network and comprises a control unit;

assigning a Flag value to each lighting panel;

allowing a user to set one or more control parameters for each lighting panel;

transceiving data corresponding to the Flag value and the one or more control parameters among the plurality of lighting panels;

detecting in the network for a change in the Flag value for each of the plurality of lighting panels;

comparing the Flag values of each of the plurality of lighting panels;

identifying a highest Flag value lighting panel among the plurality of lighting panels; and adopting, by each lighting panel, the one or more control parameters associated with the highest Flag value lighting panel.

19. The method of claim 18, wherein assigning the Flag value includes one of:

manually assigning the Flag value in response to an input from a button;

automatically updating the Flag value when a user modifies at least one of the one or more control parameters; or assigning a separate Flag value for each one or more control parameters, and automatically updating the corresponding Flag value in response to a modification of the associated one or more control parameters to each of the lighting panel.

20. The method of claim 18, further comprising:

assigning a Group ID to each of the plurality of lighting panels using the control unit;

transceiving the data corresponding to the Group ID, the Flag value, and the one or more control parameters for the lighting panel using the connection interface;

monitoring, within the network, the Flag values of each of the plurality of lighting panels in the same group to identify a highest Flag value lighting panel; and updating the control parameters of each of the plurality of lighting panels with the control parameters associated with highest Flag value lighting panel.

21. A method for controlling a plurality of lighting panels within a network, the method comprising:

connecting the plurality of lighting panels in the network, each of the plurality of lighting panels having one or more light sources, a control unit, and a connection interface to form the network wherein each of the plurality of lighting panels acts as a node;

assigning a Group ID in each of the plurality of lighting panels using the control unit such that each of the plurality of lighting panels having same value of the Group ID is assigned to a same group;

setting one or more control parameters using the control unit, wherein each of the one or more control parameters is associated with a Flag value;

monitoring, within the network, the Flag values of each of the one or more control parameters of each of the plurality of lighting panels in the same group;

identifying a highest Flag value lighting panel for each of the one of the one or more control parameters; and updating the one of the one or more control parameters of each of the plurality of lighting panels with a value associated with the highest Flag value lighting panel.

* * * * *